US00PP12057P2

(12) United States Plant Patent
Zaiger et al.

(10) Patent No.: US PP12,057 P2
(45) Date of Patent: Aug. 14, 2001

(54) NECTARINE TREE NAMED 'RED ROY'

(76) Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/499,116

(22) Filed: Feb. 7, 2000

(51) Int. Cl.[7] ..... A01H 5/00
(52) U.S. Cl. ..... Plt./190
(58) Field of Search ..... Plt./190

(56) References Cited

U.S. PATENT DOCUMENTS

P.P. 8,084 * 1/1993 Taylor ..... Plt./190
P.P. 8,255 * 6/1993 Jackson et al. ..... Plt./190
P.P. 8,948 * 10/1994 Bradford et al. ..... Plt./190
P.P. 10,250 * 2/1998 Zaiger et al. ..... Plt./190

* cited by examiner

*Primary Examiner*—Bruce R. Campell
*Assistant Examiner*—Susan B. McCormick

(57) ABSTRACT

Our new and distinct variety of nectarine tree (*Prunus persica* var. *nucipersica*), its novelty consists of the following unique combination of desirable features that are outstanding in a new variety. The features of the tree and its fruit are characterized with the tree budded on 'Nemaguard' Rootstock (non-patented), grown on Hanford sandy loam soil with Storie Index rating 95, in USDA Hardiness Zone 9, near Modesto, Calif., and with standard commercial cultural fruit growing practices, such as, pruning, thinning, spraying, irrigation and fertilization:

1. Heavy and regular production of early maturing, large size fruit.
2. Fruit with a high degree of attractive red skin color.
3. Fruit with firm flesh, good handling and shipping quality.
4. Fruit with good flavor and eating quality.
5. Having a low winter chilling requirement of approximately 350 hours below 45° F.
6. Relatively uniform size fruit throughout the tree.
7. Vigorous upright growth.

1 Drawing Sheet

BACKGROUND OF THE VARIETY

In the field of plant genetics we conduct an extensive and continuing plant-breeding program including the origination and asexual reproduction of orchard trees, and of which plums, peaches, nectarines, apricots, cherries and interspecifics are exemplary. It is against this background of our activities that the present variety of nectarine tree was originated and asexually reproduced by us in our experimental orchard located near Modesto, Stanislaus County, Calif.

PRIOR VARIETIES

Among the existing varieties of nectarines know to us, and mentioned herein; 'May Glo' Nectarine (U.S. Plant Pat. No. 5,245) and 'Ruby Gold' Nectarine (U.S. Plant Pat. No. 3,101).

ORIGIN OF THE VARIETY

The present new variety of nectarine tree was developed by us in our experimental orchard located near Modesto, Calif., as a third generation cross between a selected seedling with the field identification number 12GA1100 (non-patented) and 'May Glo' Nectarine (U.S. Plant Pat. No. 5,245). The genetic dwaft nectarine seedling selection 12GA1100, which is the maternal parent, was selected as an addition to our gene pool to be used in our breeding program, orginated as a second-generation seedling that was selected from a cross between a genetic dwarf nectarine seedling of unknown parentage and 'Ruby Gold' Nectarine (U.S. Plant Pat. No. 3,101). A large group of these third generation seedlings were grown and maintained, on their own root system. One seedling, which is the present variety, exhibited especially desirable fruit characteristics and was selected for asexual reproduction and commercialization.

ASEXUAL REPRODUCTION OF THE VARIETY

Asexual reproduction of the new and distinct variety of nectarine tree was by budding to 'Nemaguard' Rootstock (non-patented), the standard rootstock for nectarine in California, as performed by us in our experimental orchard located near Modesto, Calif., and shows that reproductions run true to the original tree and all characteristics of the tree and its fruit are established and transmitted through succeeding asexual propagations.

SUMMARY OF THE VARIETY

A new and distinct variety of nectarine tree, which is of large size, vigorous, upright growth and a regular and productive bearer of large, firm, yellow flesh, clingstone fruit with good flavor and eating quality. The tree has a low winter chilling requirement of approximately 350 hours and has the ability to produce high quality fruit in the southern areas of the United States. The tree produces relatively uniform size fruit throughout the tree with a high degree of red skin color, and firm flesh with good handling and shipping quality. In comparison to the 'May Glo' Nectarine (U.S. Plant Pat. No. 5,245), the new variety requires approximately 50 hours more winter chilling, is more upright in growth, produces fruit that is larger in size and is approximately 3 to 4 days later in maturity. In comparison to its parent '12GA1100', which is a genetic dwarf, the new variety is standard in height and growth, the fruit has improved quality, a higher degree of red skin color and matures approximately 7 weeks earlier.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of nectarine tree, age of 6 years, budded to 'Nemaguard' Rootstock (non-patented), its flowers, foliage and fruit, as based on observations of specimens grown near Modesto, Calif., with color terminology (except those in common terms) in accordance with Reinhold Color Atlas by A. Kornerup and J.H. Wanscher.

Tree:

*Size.*—Large. Pruned 12 to 14 feet in height at maturity for economical harvesting of fruit.

*Vigor.*—Vigorous. Growing 6 to 8 in height the first growing season. Pruned to 3 to 4 feet in height the first dormant season and primary scaffolds are selected for desired tree structure.

*Productivity.*—Productive. Fruit set varies from two to several times more than desired tree crop load. Fruit set is spaced and thinned to develop into desired market size fruit. Number of fruit set varies with climatic conditions and cultural practices during bloom period.

*Bearer.*—Regular. Fruit set has been heavy and thinning was necessary the past 6 years.

*Form.*—Upright, pruned to vase shape.

*Density.*—Medium dense. Pruning the branches from the center of the tree to obtain vase shape allows for air movement and sunlight to enhance fruit color and fruit wood growth throughout the tree.

*Hardiness.*—Tree grown in USDA Hardiness Zone 9. Winter chilling requirement is approximately 350 hours below 45° F.

Trunk:

*Size.*—Large. Age of tree 6 years. Circumference 17 inches, measured 12 inches from ground. Varies slightly with type of soil and cultural practices.

*Texture.*—Medium shaggy. Varies slightly with age of tree.

*Color.*—Brown to beaver brown (5-E-2) to (5-F-2), varies with age of tree.

Branches:

*Size.*—Medium, average circumference of 8 inches measured 41 inches above ground. Varies with age of tree.

*Texture.*—Smooth to medium rough, varies with age of growth.

*Lenticels.*—Few in number. Medium in size, average number of 22 within a 4 square inch surface. Average length 3/32 inch. Average width 1/16 inch. Size of lenticels increase as size of branches become larger. Color — yellowish brown to light brown (5-D-4) to (5-D-6).

*Color.*—First year's new growth, bile yellow to spring green (30-C-5) to (30-C-8). Older mature growth, hair brown to linoleum brown (5-E-4) to (5-E-7), varies with age of growth.

Leaves:

*Size.*—Large. Average length 5¼ inches. Average width 1⅜ inches.

*Form.*—Lanceolate.

*Apex.*—Acuminate.

*Base.*—Cuneate.

*Margin.*—Crenate.

*Thickness.*—Medium.

*Surface.*—Upper surface smooth. Lower surface relatively smooth except for small ridges created by midvein with pinnate venation. Veining color — pale yellowish green to greenish yellow (30-B-5) to (30-B-6).

*Petiole.*—Medium size. Average length ½ inch. Average width 5/64 inch, grooved longitudinally. Color — bile yellow to lettuce green (30-D-5) to (30-D-7).

*Glands.*—Number varies from 0 to 4. Average number 2. Reniform. Color — sap green to spring green (30-B-7) to (30-C-7), varies with age of leaf. Located on the lower portion of the leaf blade and on the upper portion of the petiole.

*Stipules.*—Average 2 per leaf bud. Average length 29/32 inch.

*Color.*—Upper surface — green to dark green (28-F-6) to (28-F-8). Lower surface — dull green to light green (28-E-6) to (28-E-8).

Flower buds:

*Size.*—Large. Average length 45/64 inch. Average width 13/32 inch. Four days before bloom.

*Form.*—Plump, free. Varies from conical to elongate as bud development progresses. Usually one bud forms on each side of a leaf bud on previous years new growth.

Flowers:

*Size.*—Large, showy. Average height 1 inch. Average diameter 1 31/64 inches.

*Petal.*—Number — 5, alternately positioned to sepals. Shape — varies from orbicular to slightly elongated as flower develops. Narrows at point of attachment. Apex — rounded, edges smooth to slightly scalloped. Base — rounded except at point of attachment. Texture — fine, delicate, smooth. Color — both surfaces relatively the same color, light pink to pink (10-A-3) to (10-A-5), with the surface exposed to the sunlight fading to a lighter color more rapidly than the surface in the shaded areas.

*Stamens.*—Number per flower — 41 to 45. Average number 43. Filament length ½ inch. Filament color — white (11-A-1). Anther color — grayish red to geranium red (11-B-50 to (11-B-7).

*Pistil.*—Number — usually 1, varies from 1 to 2. Average length 45/64 inch. Surface — glabrous. Color — pale yellow to grayish yellow, (2-B-5) to (2-B-6), color fades as flower ages. Stigma is 3/32 inch higher than anthers.

*Sepals.*—Number — 5. Average length 7/32 inch. Average width 11/64 inch. Alternately arranged with petals. Shape — elongated, apex rounded. Upper surface — glabrous. Lower surface — pubescent. Color — upper surface — olive green to moss green (1-E-6) to (1-E-7). Lower surface grayish red to violet brown (10-E-4) to (10-E-6).

*Aroma.*—Very slight.

*Pollen.*—Present, self-fertile. Color — varies from light yellow to cream yellow (3-A-3) to (4-A-3).

*Blooming period.*—Date of First Bloom Feb. 14, 1999. Date of Last Bloom Feb. 21, 1999. Varies slightly with climatic conditions.

*Color.*—Pink to light pink (10-A-3) to (10-A-5). Color fades wtih age of flowers.

Fruit:

*Maturity when described.*—Firm ripe (shipping ripe).

*Date of first picking.*—Jun. 1, 1999.

*Date of last picking.*—Jun. 7, 1999. Varies slightly with climatic conditions.

*Size.*—Average diameter axially 2 15/16 inches. Average transversely in suture plane 2 7/8 inches. Average weight 212 grams. Average size and weight varies slightly with fertility of the soil, amount of thinning and climatic conditions.

*Form.*—Nearly globose, slightly elongated.

*Suture.*—Shallow, slightly lipped, runs from base to apex.

*Ventral surface.*—Slightly indented.

*Apex.*—Varies from rounded to slight apical point.

*Base.*—Retuse.

*Cavity.*—Rounded to slightly elongated in suture plane. Average depth ½ inch. Average breadth 1 inch.

Skin:

*Thickness.*—Medium, tenacious to the flesh.

*Texture.*—Medium, slight roughness to surface, shows no scarring or discoloration during picking or packing trials of fruit. Taste — non-astringent.

*Tendency to crack.*—None.

*Color.*—Yellow to golden yellow (4-A-7) to (4-A-8) ground color. Overspread with red to signal red (10-A-8) to (10-B-8).

Stem:

*Size.*—Average length 7/16 inch. Average diameter 1/8 inch.

*Color.*—Yellowish green to spring green (30-B-6) to (30-C-7).

Flesh:

*Ripens.*—Evenly.

*Texture.*—Firm, meaty.

*Fibers.*—Few, small, tender.

*Aroma.*—Very slight.

*Amygdalin.*—Undetected.

*Eating quality.*—Good.

*Flavor.*—Good.

*Juice.*—Moderate.

*Brix.*—10.6°, varies slightly with number of fruit per tree, cultural practices and climatic conditions at maturity.

*Color.*—Butter yellow to sunflower yellow (4-A-5) to (4-A-7). Pit cavity — grayish yellow to amber yellow (4-B-4) to (4-B-7).

Stone:

*Type.*—Clingstone.

*Size.*—Large. Average length 1½ inches. Average width 1⅛ inches. Average thickness 13/16 inch.

*Form.*—Obovoid.

*Base.*—Usually rounded, varies from rounded to straight.

*Apex.*—Acute, short.

*Surface.*—Irregularly furrowed toward apex, pitted toward base. Pits vary from round to elongated. One long furrow on each side of suture.

*Sides.*—Equal to unequal, some stones are slightly larger on one side.

*Ridges.*—Surface varies from sharp to rounded.

*Tendency to split.*—Slight.

*Color.*—Light brown to brown (5-C-6) to (5-D-7).

Use: Market. Local and long distance.

Keeping quality: Good. Fruit held firm in cold storage (38° to 42° F.) for 3 weeks without internal browning or wooliness of flesh.

Shipping quality: Good. Fruit showed minimal bruising of flesh or skin scarring after packing and shipping trials.

Disease resistance susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics, with abnormal fungus, bacterial, virus, or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, characterized by its large size, vigorous, upright growth and a regular and productive bearer of large, early maturing, firm, yellow flesh, clingstone fruit with good flavor and eating quality; the tree is further characterized by having a low winter chilling requirement of approximately 350 hours, producing fruit with good storage and shipping quality and in comparison to the low chilling nectarine 'May Glo' (U.S. Plant Pat. No. 5,245), the tree is more upright in growth and the fruit is larger in size and approximately 3 to 4 days later in maturity.

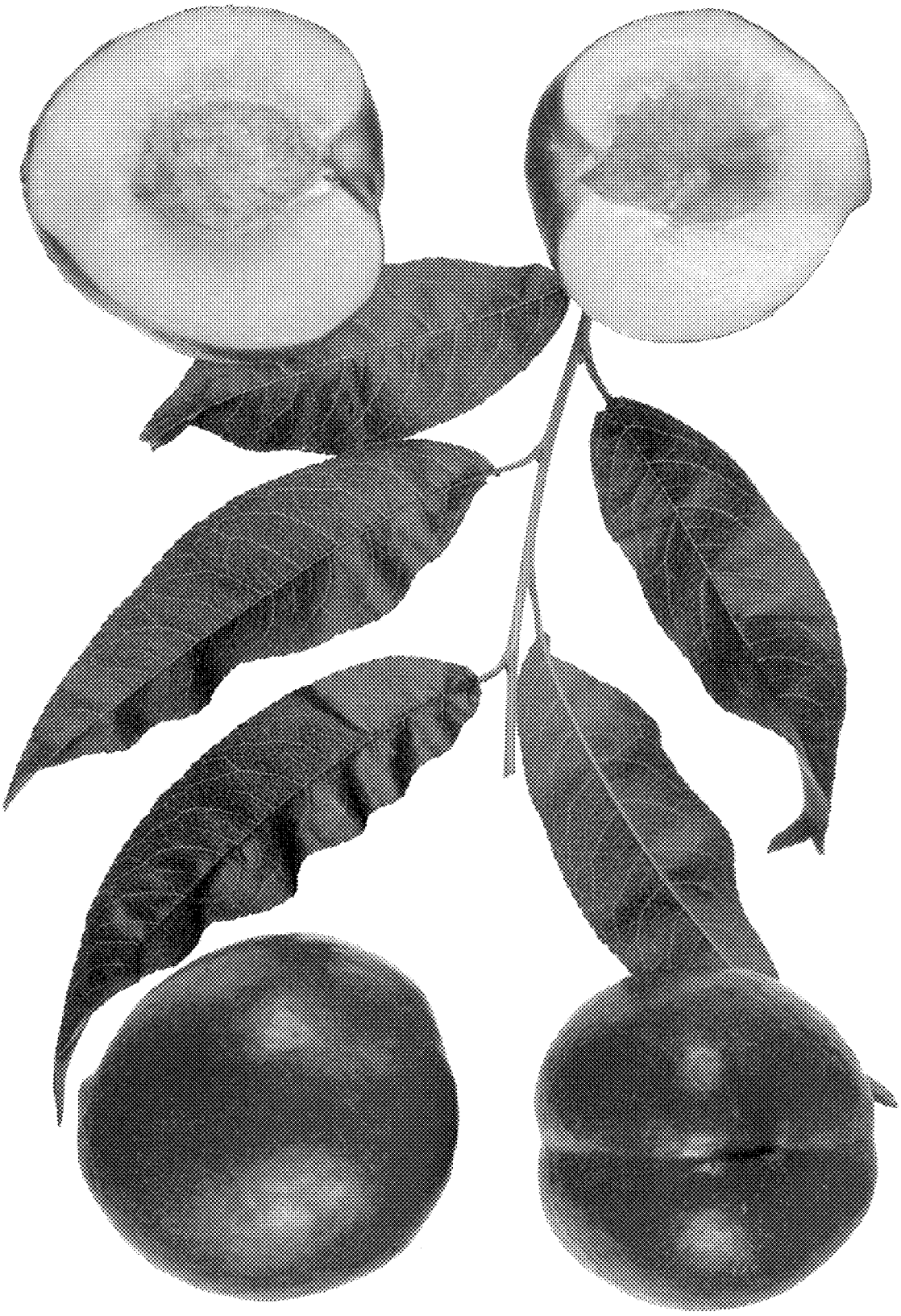

* * * * *